United States Patent
Caserta et al.

(10) Patent No.: US 7,209,650 B2
(45) Date of Patent: Apr. 24, 2007

(54) METHOD AND DEVICE FOR THE EVAPORATION OF VOLATILE COMPOUNDS

(75) Inventors: Andrea Caserta, Cerdanyola Del Valles (ES); Pere Casas Colomer, Cerdanyola Del Valles (ES); Ruben Garcia Fabrega, Cerdanyola del Valles (ES)

(73) Assignee: DBK Espana, S.A., Barcelona (ES)

( * ) Notice: Subject to any disclaimer, the term of this patent is extended or adjusted under 35 U.S.C. 154(b) by 0 days.

(21) Appl. No.: 10/813,181

(22) Filed: Mar. 29, 2004

(65) Prior Publication Data

US 2005/0213948 A1    Sep. 29, 2005

(51) Int. Cl.
*F24F 6/08* (2006.01)
(52) U.S. Cl. .................................. 392/395; 392/387
(58) Field of Classification Search ................ 392/386, 392/387, 390, 391, 392, 394, 395; 239/34, 239/44, 50
See application file for complete search history.

(56) References Cited

U.S. PATENT DOCUMENTS

| | | | | |
|---|---|---|---|---|
| 1,994,932 | A * | 3/1935 | Lucien | 422/122 |
| 4,874,924 | A * | 10/1989 | Yamamoto et al. | 392/395 |
| 4,968,487 | A | 11/1990 | Yamamoto et al. | 422/125 |
| 6,285,830 | B1 * | 9/2001 | Basaganas Millan | 392/395 |
| 6,563,091 | B2 * | 5/2003 | Vieira | 219/486 |
| 6,917,754 | B2 * | 7/2005 | Pedrotti et al. | 392/395 |

FOREIGN PATENT DOCUMENTS

| | | |
|---|---|---|
| EP | 0 942 648 B1 | 1/2002 |
| EP | 1 283 062 A1 | 2/2003 |
| ES | 2 137 111 | 12/1999 |
| ES | 2 185 490 | 4/2003 |

OTHER PUBLICATIONS

International Search Report dated Jun. 11, 2004.
Written Opinion of the International Preliminary Examining Authority issued Feb. 13, 2006 in corresponding PCT Application No. PCT/ES2004/000139.

* cited by examiner

*Primary Examiner*—Sang Y. Paik
(74) *Attorney, Agent, or Firm*—Ostrolenk, Faber, Gerb & Soffen, LLP

(57) ABSTRACT

A method and a device to evaporate volatile substances such as aromatic substances and/or insecticides, in which the volatile substances are evaporated using electrical heating devices that heat a wick impregnated with the substance to be evaporated. The method and device permits the evaporation of the volatile substance efficiently by optimizing the use of heat energy generated by electrical heating devices. The device comprises a rotating pipe with at least one opening with a portion of wick inserted in this pipe and depending on the position of this pipe relative to the heating elements, the amount of heat flow transmitted to the wick is regulated as well as, consequently, the degree of evaporation of the volatile substance.

15 Claims, 6 Drawing Sheets

METHOD AND DEVICE FOR THE EVAPORATION OF VOLATILE COMPOUNDS

OBJECT OF THE INVENTION

Figure 1:
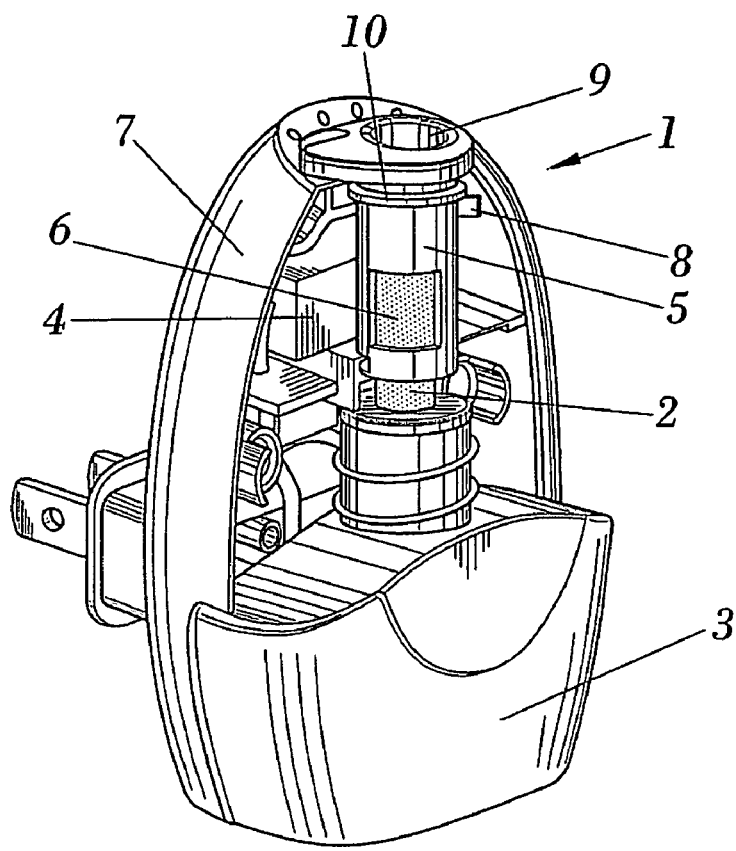
Figure 1:
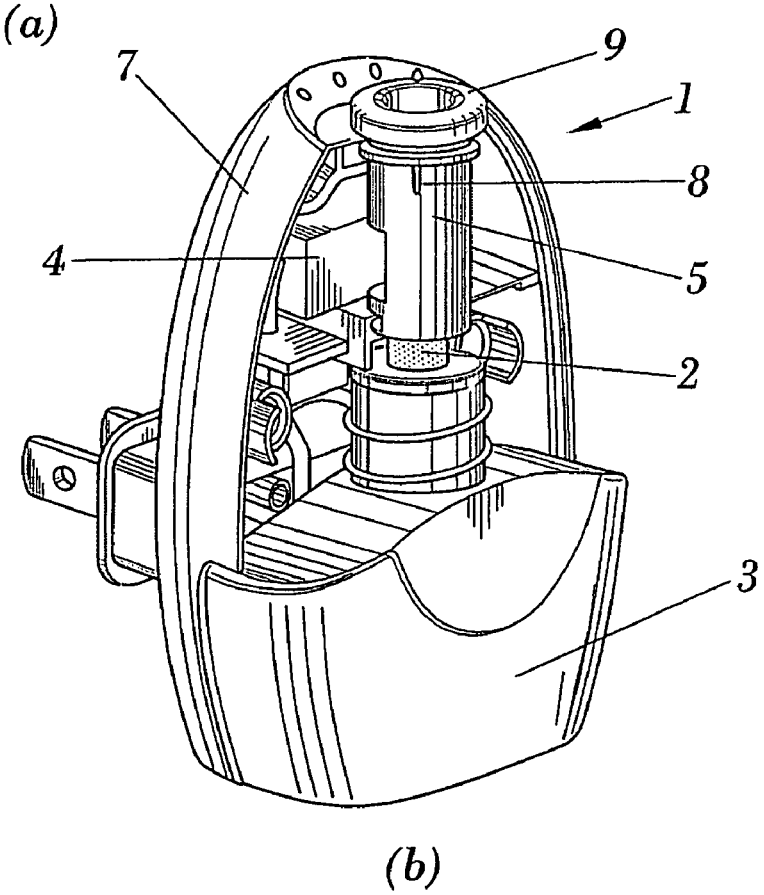

The present invention is related with a method and a device for the evaporation of volatile substances such as aromatic substances and/or insecticides, in which the evaporation is done by electrical heating devices that raise the temperature of a wick impregnated with the substance to be evaporated.

With this invention the degree of evaporation of the volatile substance can also be controlled.

BACKGROUND OF THE INVENTION

Devices to evaporate volatile substances in a liquid state are well known that consist of a wick of which one end is in contact with a volatile substance in a bottle, such that the substance rises by capillarity through the wick, which is made of a porous material, until this becomes totally impregnated.

Conventionally, these devices include heating devices, such as PTC electrical resistances, aimed at heating the upper portion of the wick that facilitates evaporation of the substance that dissipates to the exterior of the device in the form of vapor.

Some of these pieces of equipment are equipped with devices that permit the degree of evaporation of the product to be controlled, which are generally based on modifying the intensity of heating the wick. The need to control the degree of evaporation tends to complicate the design and manufacture of the device since several interconnecting parts are required, making the manufacturing process more expensive, which is a key factor in these products since the low production costs are the key to their profitability.

Some known devices of this kind use heating elements with a toroidal configuration such that one end of the wick is lodged in the central orifice, permitting uniform heating of the whole perimeter of the wick in the area of influence of the heating element. Although this toroidal shape of the heating element is effective from an operative perspective, the device as a whole increases in width and, therefore, size and this is undesirable from manufacturing and sales perspectives.

Some examples of this type of device can be found in the patents U.S. Pat. No. 4,739,928, EP-1.270.022, U.S. Pat. No. 6,659,301.

DESCRIPTION OF THE INVENTION

The present invention refers to a method and a device for the evaporation of volatile substances that optimally exploits the heat energy generated.

In addition to the afore-mentioned advantages, with this invention the user can control at will the degree of evaporation of the substance and achieves this using a single element that maximally simplifies the manufacturing process and the cost of the product.

Therefore, one of the aspects of the invention refers to a device for the evaporation of volatile substances that includes a wick through which this substance travels upwards by capillarity, which is influenced by heating elements that facilitate this evaporation. The device has a pipe with open ends that contains part of the wick, with a space around the wick between this and the sides of the tube.

The pipe has at least one opening in the side that controls the degree of exposure of the wick to the focus of heat produced by the heating devices.

In this way, part of the heat generated by the heating devices passes to the chamber inside the pipe that contains part of the wick. The pipe reduces the volume of space surrounding the wick, thus less heat energy is required to obtain the degree of evaporation desired. This reduced volume facilitates a "chimney effect", i.e. an increased rate of release of the evaporated fragrance, which causes increased diffusion of the product.

The invention incorporates features that enable the user to control the degree of evaporation of the substance by controlling the degree of influence of heat on the wick.

Another aspect of the invention refers to a method to evaporate volatile substances that includes submitting a wick impregnated with the volatile substance to be evaporated to a heat source that consists in inserting part of the wick into a small-volumed chamber and introducing hot air into the chamber. Reduced volume refers to a chamber with a volume slightly larger than that of the portion of wick inside it, such that there is a narrow space around the wick between this and the sides of the pipe through which the hot air can rise.

This chamber consists of a tubular pipe, open at both ends, which has at least one lateral opening such that in the method of the invention hot air produced by the heat source is introduced through this lateral opening of the pipe and spreads throughout the interior of the chamber remaining in close proximity to the wick while it rises up through the pipe.

In the method, the amount of hot air introduced in the chamber can be changed in order to control the degree of evaporation.

In a preferred option of the method, the amount of air is controlled by moving the position of the pipe relative to the heat source so that the opening faces the heat source to a greater or lesser degree thus resulting in a greater or lesser transfer of radiation and convection to the inside of the pipe and to the surface of the wick exposed to the heat.

DESCRIPTION OF THE DIAGRAMS

Complementary to the description given here this is accompanied, as an integral part of this description, by a set of diagrams, of an illustrative and not restrictive nature, aimed at helping to clarify the characteristics of the invention in accordance with an example of a practical application of this invention. These diagrams represent the following:

FIG. 1.–FIG. 1a shows a view, in perspective, of the evaporation device without the front part of its casing, in which the pipe is in the position corresponding to minimum evaporation, while FIG. 1b shows a similar representation of the previous diagram but in which the pipe is in the position corresponding to maximum evaporation.

Figure 2:
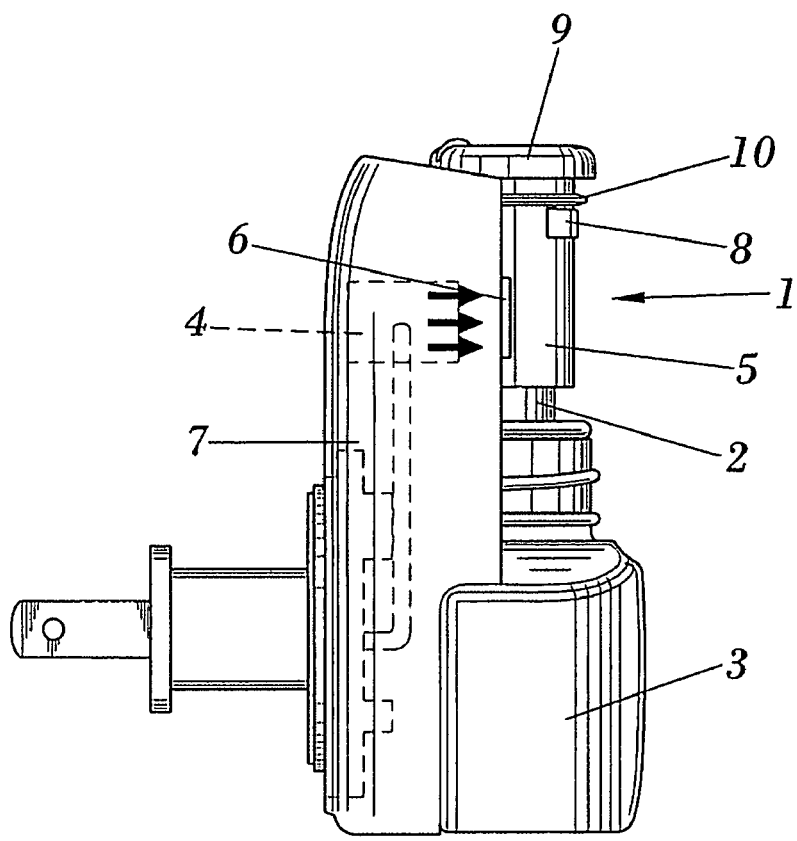
Figure 2:
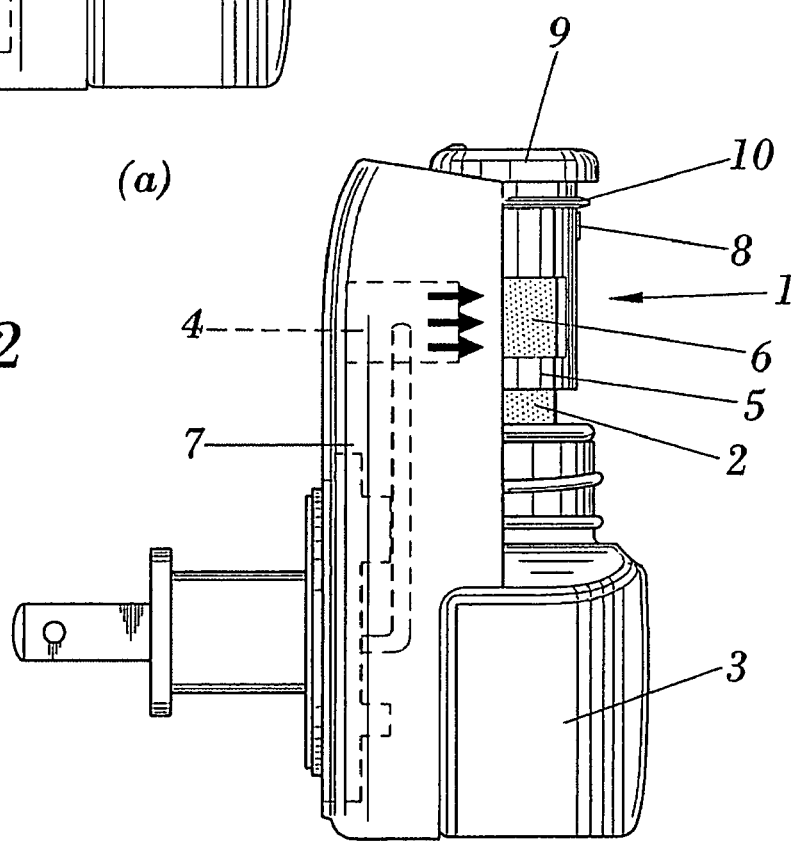

FIG. 2.–FIG. 2a shows a side view of the evaporation device without the front part of its casing, in which the pipe is in the maximum evaporation position while FIG. 2b shows a similar representation to that of the previous figure but in which the pipe is in the minimum evaporation position. In both figures, the heat generated by the heating elements is represented by three black arrows.

Figure 3:
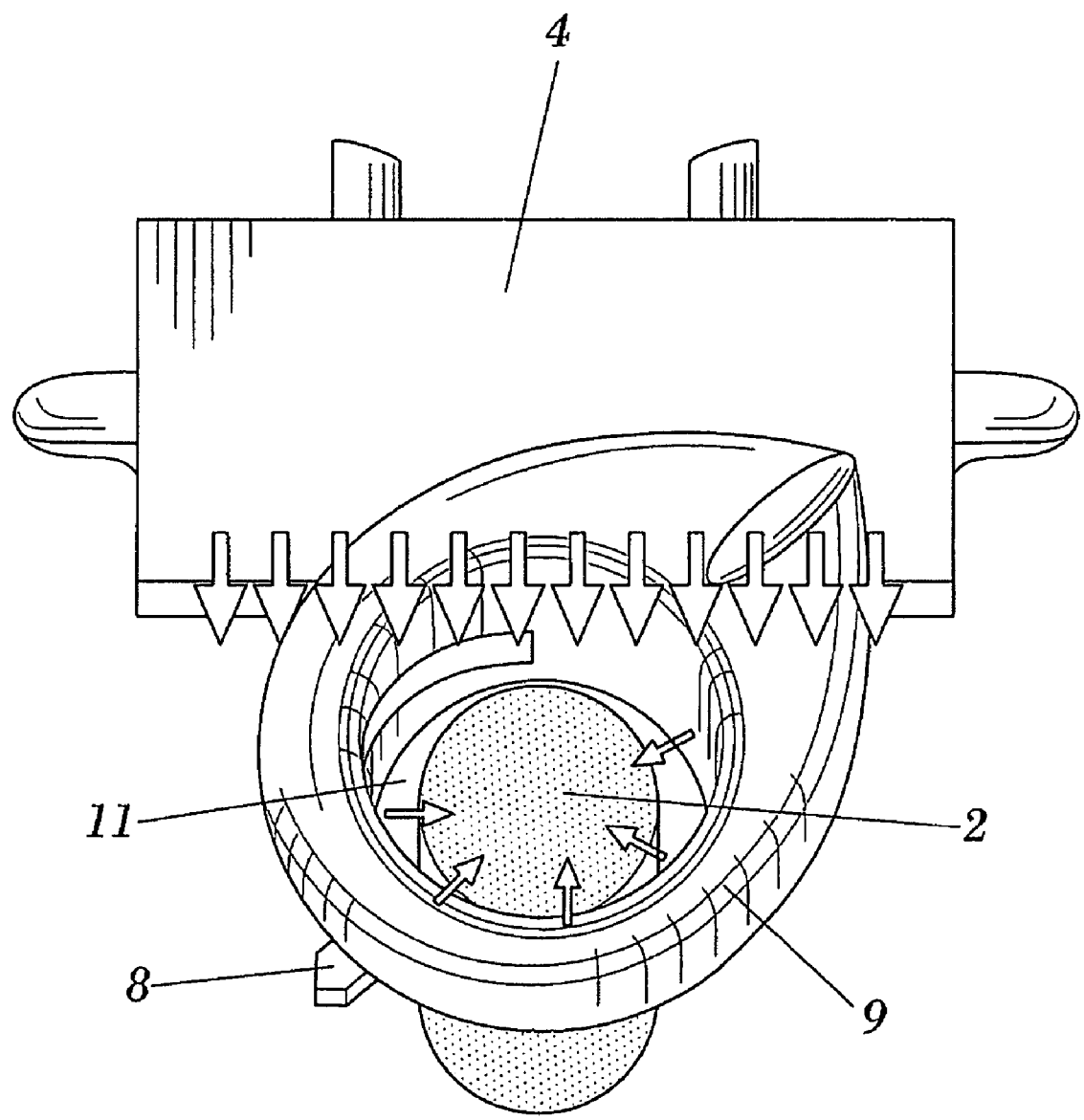

FIG. 3—shows a diagram, in perspective, of the wick, the pipe in which it is inserted and the heating elements, where the direction of heat radiated is represented by arrows.

Figure 4:
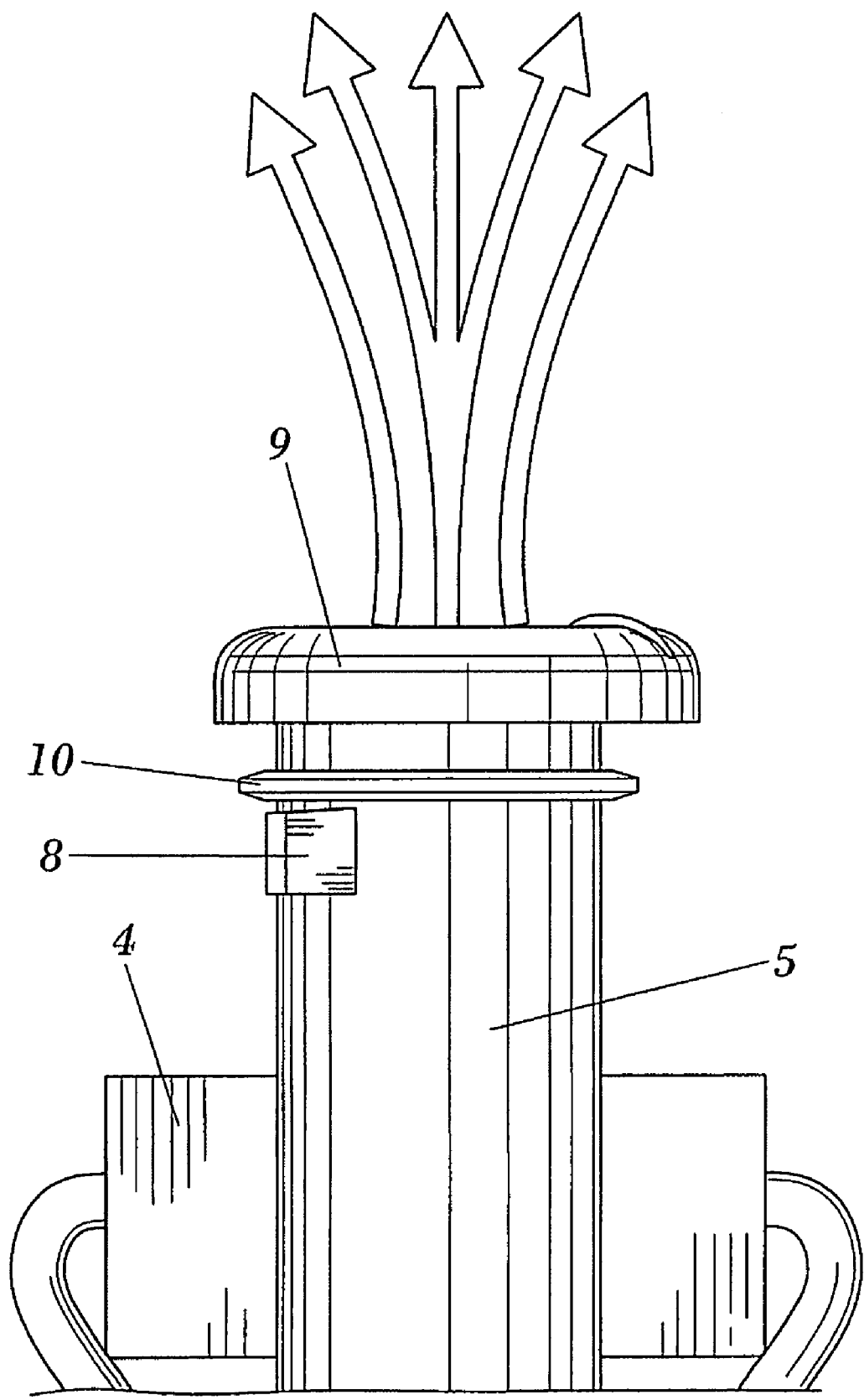

FIG. 4.—shows a similar diagram to the previous one showing a frontal view of the same parts. The figure reveals an improved exit of the convective flow (a smaller cross-sectional area results in increased exit speed and, therefore, greater range).

Figure 5:
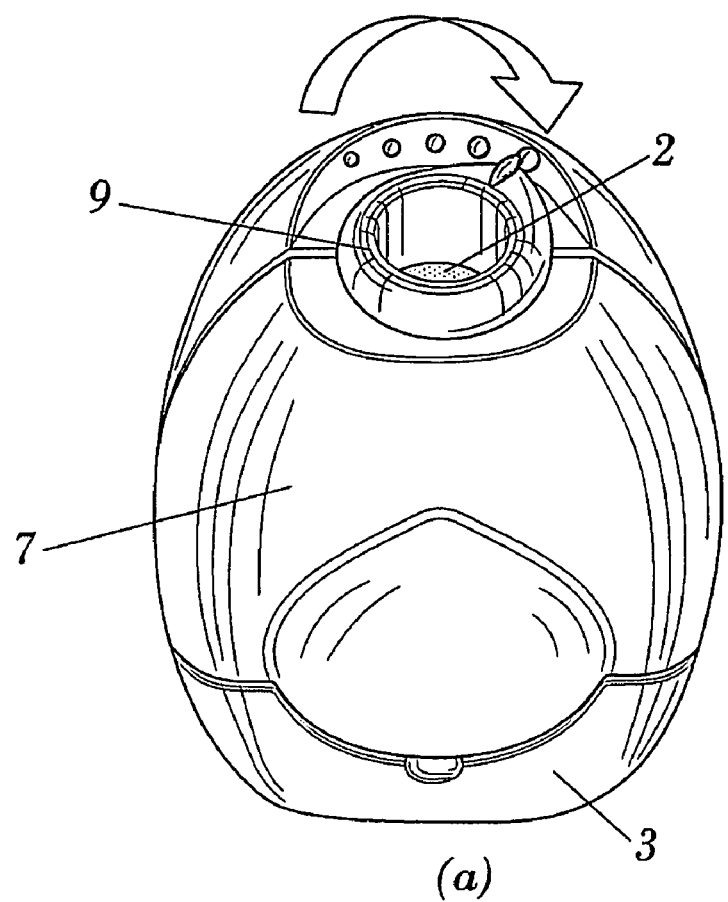
Figure 5:
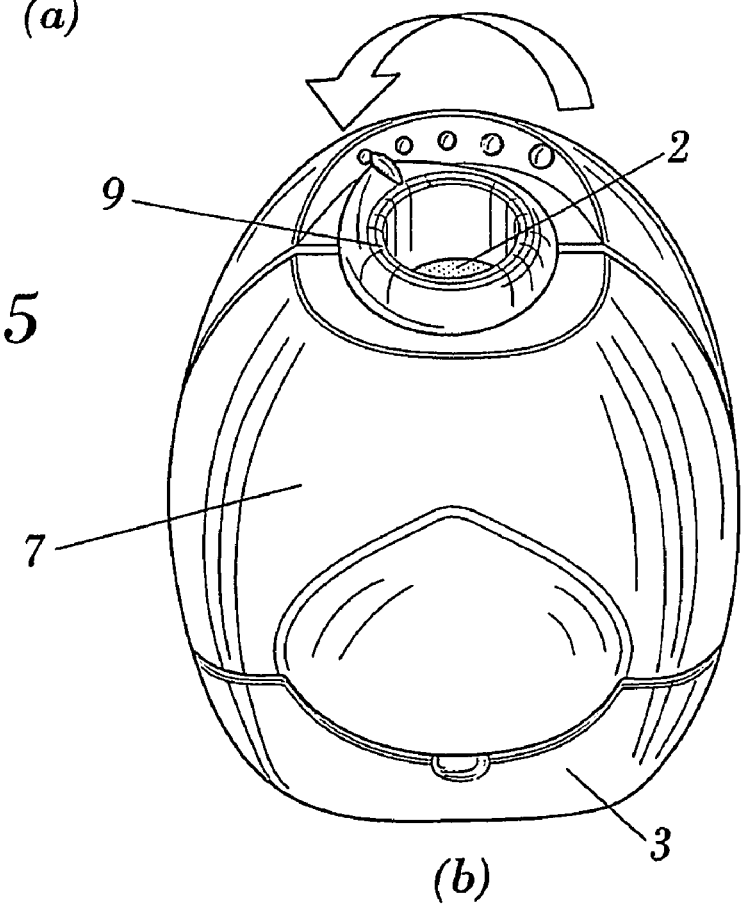

FIG. 5.—shows both views of the evaporation device, in perspective, with its graduated evaporation scale of which FIG. 5a shows the device in the maximum evaporation position and FIG. 5b the device in the minimum evaporation position.

Figure 6:
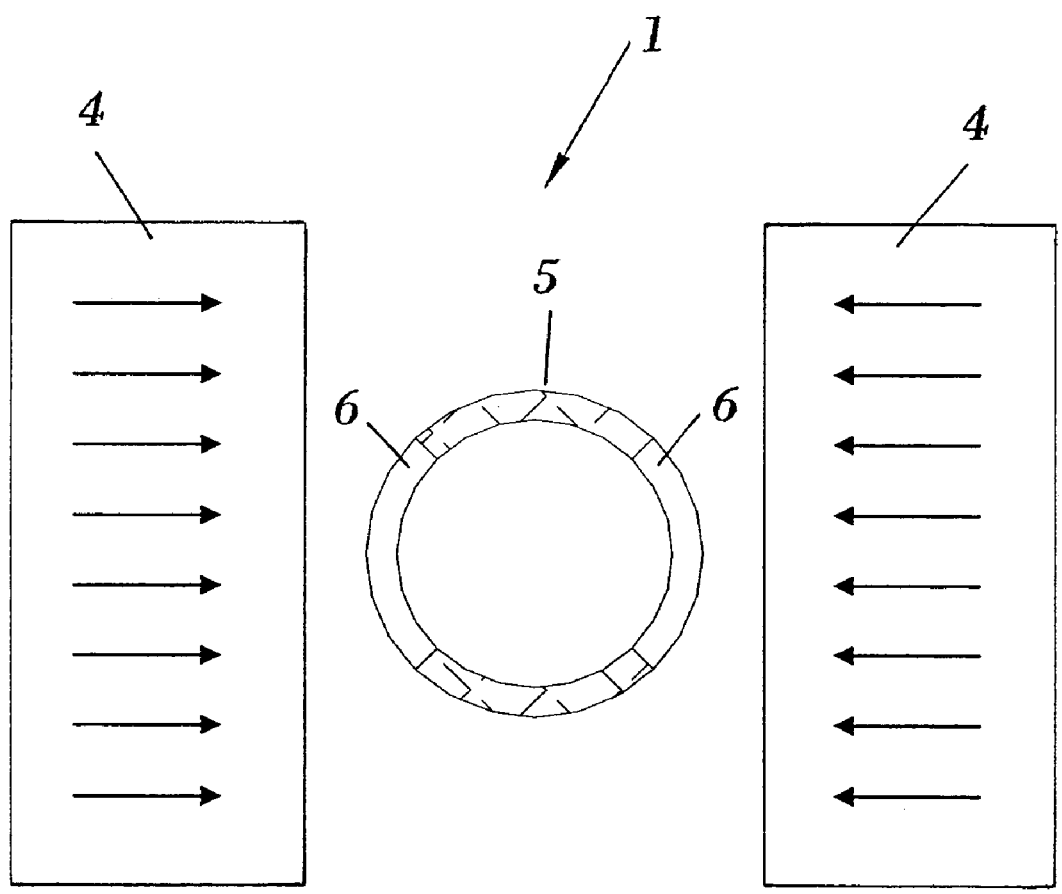

FIG. 6.—is a view, partially in section, showing an embodiment of the evaporation device with a heating element comprising two resistances positioned diametrically to the pipe, wherein the pipe is provided with two lateral openings and wherein the heat generated by the heating elements is represented by the black arrows.

PREFERABLE IMPLEMENTATION OF THE INVENTION

In the light of the figures described it can be observed how in one of the possible implementations of the invention, device (1) includes a wick (2) the lower end of which is submerged inside a bottle (3) that contains the substance to be evaporated in a liquid state, which impregnates the whole wick (2). The heating elements (4) consisting for example of a cemented resistance are located near the upper part of the wick (2) heating this region.

The device (1) of the invention consists of a cylindrical pipe (5) which contains a portion of the wick (2).

The pipe (5) has an opening (6) in the side, and is fitted into a casing (7) that forms part of the device (1), on which it can rotate in one plane, i.e. it is free to rotate on its axis but can not be displaced vertically. The resistance (4) is firmly attached to the casing (7), thus rotation of the pipe (5) changes the position of the opening (6) relative to the resistance (4) and, therefore, changes the heat flow transmitted to the wick in the pipe (5).

In another preferable application (as shown in FIG. 6), the device (1) can have two small resistances (4) situated on each side of the pipe (5) which, in turn, would have two openings (6), which could reduce even further the dimensions of the device and produce a more uniform heating of the wick since the hot air would affect opposite sides of the device.

The resistances used are flat in order to occupy the smallest possible space inside the casing (7), as can be seen in FIG. 2. This same FIG. 2 shows how the resistance (4) is located in the same plane, i.e. at the same height as the opening (6), so that the heat generated by it reaches the wick more directly (2) and more heat enters the pipe (5). In the different positions of the pipe (5), the position and distance of the opening are modified (6) relative to the resistance (4), which, in turn, alters the surface of the wick that directly receives the heat from the resistance (4).

In this way, two extreme positions are established in the pipe position (5), these are limited by the contact of a flange (8) attached to the pipe (5), with catches to limit rotation of the pipe on the inside of the casing (7). Therefore, a first minimum evaporation position can be defined, as can be observed in FIG. 1a and FIG. 2b, in which the opening (6) is not facing the resistance (4) and, therefore, the entrance of hot air through the opening (6) is minimal or practically nil.

In a second extreme position of maximum evaporation represented in FIGS. 1b and 2a, the entire length of the opening (6) is opposite the resistance (4), thus the intake of hot air into the pipe (5) through the opening (6) is maximum.

FIG. 3 shows how the hot air that enters the pipe (5), is distributed radially around the length of the wick (2) as it rises through the perimetric space (11), until it leaves the pipe as in FIG. 4.

The upper end of the pipe (5) emerges from the upper end of the casing (1) forming a ring-shaped protuberance (9) facilitating manual handling by the user. For this purpose, the pipe (5) has a lip on its perimeter (10) that overlaps an internal part of the casing (1), which can be found between this lip (10) and the ring-shaped protuberance (9), preventing displacement of the pipe (5) vertically but permitting it to rotate.

In the light of this description and set of figures, an expert in the area can understand that the description of the invention corresponds to preferential implementations but that multiple variations can be introduced that would not be outside the scope of the invention as this appears in the claims.

The invention claimed is:

1. Device for the evaporation of volatile substances that includes a wick which the substance travels up by capillarity, the wick being affected by heating elements that facilitate evaporation of the volatile substance, said device comprising a tubular pipe with open ends which contains an upper part of the wick, wherein a perimetric chamber is defined around the wick between said upper part of the wick and the pipe, in such a manner that a chimney effect can be created in said perimetric chambers wherein the pipe has at least one lateral opening that permits a flow of heat from the heating elements to the wick, wherein the heating elements are fixed and the pipe rotates in one plane and whereupon, upon rotational movement of the pipe a first extreme minimum evaporation position is defined in which the opening is not facing the heating elements and a second maximum evaporation position is also defined in which the opening faces these heating elements, said device further including a casing, wherein the heating elements and the pipe are supported by said casing and wherein an upper end of the pipe juts out of the top of the casing, forming an annular protuberance that facilitates manual movement of the pipe relative to the casing.

2. Device according to claim 1 wherein the heating elements and the pipe can move relative to each other and wherein this relative movement can alter a degree of overlap between the wick and the heating elements and, consequently, the amount of heat reaching the wick.

3. Device according to claim 1 wherein the heating elements comprise at least one electrical resistance located close to the wick.

4. Device according to claim 3 wherein the resistance forms at least one plane surface.

5. Device according to claim 3 wherein the resistance is of prismatic rectangular shape.

6. Device according to claim 1 wherein the heating elements comprise two resistances positioned diametrically to the pipe and wherein the pipe has two lateral openings.

7. Device according to claim 6 wherein the resistances form at least one plane surface.

8. Device according to claim 6 wherein the resistances are of prismatic rectangular shape.

9. Device according to claim 1 wherein the heating elements and the at least one lateral opening of the pipe are in the same plane, such that part of the wick can face the heating element through the at least one lateral opening.

10. Device according to claim 1 wherein the pipe has a perimetric lip and wherein a portion of the casing is located between this perimetric lip and an annular protuberance on the pipe, preventing vertical displacement of the pipe but permitting the pipe to rotate.

11. Device according to claim 1 wherein the pipe is cylindrical.

12. Device according to claim 1 wherein the volatile substance is at least one of an aromatic substance and an insecticide.

13. Device according to claim 1 wherein the heating element is located at a lower level than said perimetric chamber, and wherein the device is arranged such that hot air can pass through said lateral opening.

14. Device according to claim 1 wherein hot air entering into said tubular pipe is distributed around the length of the wick as the hot air rises through the perimetric space, until said hot air leaves the pipe.

15. Method of evaporation of volatile substances that includes applying a heat source to a volatile substance to be evaporated from a wick, said method comprising enclosing a portion of the wick in a small volumed chamber, said chamber having at least one lateral opening, and introducing hot air into the chamber through said at least one lateral opening, wherein the chamber is formed of a tubular pipe with open ends and wherein the hot air is introduced through a side opening in the pipe and wherein the amount of hot air entering the chamber is regulated by displacement of the pipe relative to the heat source by modifying the distance between the side opening and the heat source, wherein said pipe is rotatable on its axis but can not be displaced vertically, said pipe and said heat source being supported within a casing, wherein an upper end of the pipe juts out of the top of the casing, forming an annular protuberance that facilitates manual movement of the pipe relative to the casing.

* * * * *